(12) United States Patent
Mahesh et al.

(10) Patent No.: US 7,787,699 B2
(45) Date of Patent: Aug. 31, 2010

(54) REAL-TIME INTEGRATION AND RECORDING OF SURGICAL IMAGE DATA

(75) Inventors: Prakash Mahesh, Schaumberg, IL (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 1159 days.

(21) Appl. No.: 11/205,632

(22) Filed: Aug. 17, 2005

(65) Prior Publication Data

US 2007/0041660 A1  Feb. 22, 2007

(51) Int. Cl.
*G06K 9/00* (2006.01)
*G06K 9/32* (2006.01)

(52) U.S. Cl. ........................ 382/232; 382/294

(58) Field of Classification Search ................ 382/100, 382/128–133, 168, 173, 181, 184, 189, 203, 382/232, 256, 270, 274, 276, 305; 434/262; 600/300, 301; 430/7; 128/901, 903, 904, 128/920–925; 705/2–3; 707/104.1, 100–103
See application file for complete search history.

(56) References Cited

U.S. PATENT DOCUMENTS

| 6,167,296 | A | 12/2000 | Shahidi |
| 6,551,243 | B2* | 4/2003 | Bocionek et al. ............ 600/300 |
| 6,574,742 | B1* | 6/2003 | Jamroga et al. ............ 713/400 |
| 2006/0072797 | A1* | 4/2006 | Weiner et al. ................ 382/128 |
| 2006/0167945 | A1* | 7/2006 | Trautner ................... 707/104.1 |
| 2006/0235936 | A1* | 10/2006 | Lei et al. ..................... 709/208 |
| 2006/0239573 | A1* | 10/2006 | Novatzky et al. ............ 382/239 |
| 2006/0251975 | A1* | 11/2006 | Taranath et al. ................ 430/7 |

FOREIGN PATENT DOCUMENTS

| CN | 1405699 A | 3/2003 |
| WO | WO 94/24631 A | 10/1994 |
| WO | WO 00/56215 A1 | 9/2000 |
| WO | 0241136 A2 | 5/2002 |
| WO | WO 02/41136 A2 | 5/2002 |

OTHER PUBLICATIONS

Stryker, Endoscopy "Integrated Operating Rooms," http://www.stryker.com/endoscopy/Products/integOpRoom/iorEndosuite.html, 2004.

(Continued)

*Primary Examiner*—Samir A. Ahmed
*Assistant Examiner*—Mehdi Rashidian
(74) *Attorney, Agent, or Firm*—McAndrews, Held & Malloy, Ltd.; Peter J. Vogel; Michael A. Dellapenna (57) ABSTRACT

Certain embodiments of the present application provide a method for imaging in a healthcare environment including receiving in an application a first feed, the first feed including historical patient image data; receiving in the application a second feed, the second feed including substantially live patient image data; and integrating in real-time in the application the first feed and the second feed to form a display representation, the display representation displayable on a display, and the display representation simultaneously including data corresponding to the first feed and the second feed.

16 Claims, 6 Drawing Sheets

OTHER PUBLICATIONS

Stryker, Communications "Video, Voice & Data Integration," http://www.stryuker.com/communications/VVandDI/vvdiNetworkHub.html, 2004.

Stryker, Communications "Video, Voice & Data Integration," http://www.stryuker.com/communications/VVandDI/VVand_DIMain.html, 2004.

Stryker, Communications "Video, Voice & Data Integration," http://www.stryuker.com/communications/VVandDI/vvdiSwitchPoint.html, 2004.

State Intellectual Property Office, P.R. China—First Office Action, Application No. 200610115029.X Jun. 5, 2009 (10 pages).

* cited by examiner

REAL-TIME INTEGRATION AND RECORDING OF SURGICAL IMAGE DATA

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present application relate generally to imaging in a healthcare environment. Particularly, certain embodiments relate to providing integrated displays of historical and substantially live images on a Picture Archiving and Communication System (PACS) workstation. Certain embodiments also relate to providing recording functionality for recording substantially live images on a PACS workstation.

Clinics, hospitals, and other healthcare facilities have come to rely more and more on computers over the last several decades. In particular, healthcare facilities employ certain types of digital diagnostic imaging modalities, such as computed tomography (CT), magnetic resonance imaging (MRI), ultrasound imaging, and X-ray imaging. Each digital diagnostic imaging modality may generate images with formats that differ from other modalities. In response to the problem of different image formats, The American College of Radiology and the National Electrical Manufacturers Association formed a joint committee in 1983 to develop a standard image format. This standard, eventually known as Digital Imaging and Communications in Medicine (DICOM): 1) promoted communication of digital image information, regardless of device manufacturer; 2) facilitated the development and expansion of Picture Archiving and Communication Systems (PACS) that may also interface with other systems of healthcare information; and 3) allowed for the creation of diagnostic information data bases that may be queried by a wide variety of devices distributed geographically.

Because of increasing convergence to the DICOM standard, the healthcare industry has seen a proliferation of PACS systems and workstations. PACS systems are networks, typically located in a healthcare facility such as a hospital. A user at a PACS workstation can access image data that complies with DICOM from a remote network location. For example, a PACS workstation can retrieve an image stored in a hard-disk archive, or from an imaging device such as an X-ray. Another benefit of PACS systems is that they are interoperable with other information systems. For example, PACS systems may interoperate with radiology information systems (RIS), or hospital information systems (HIS).

PACS systems and workstations have been increasingly appearing in diverse locations within a healthcare facility. For example, PACS workstations may be used various healthcare workspaces, such as radiology or surgery. Three U.S. Patent Applications filed on Oct. 1, 2004, and entitled "SYSTEM AND METHOD FOR HANDLING MULTIPLE RADIOLOGY APPLICATIONS AND WORKFLOWS," Ser. No. 10/956,434, "SYSTEM AND METHOD FOR RULES-BASED CONTEXT MANAGEMENT IN AN MEDICAL ENVIRONMENT," Ser. No. 10/956,171, and "METHOD AND APPARATUS FOR SURGICAL OPERATING ROOM INFORMATION DISPLAY GAZE DETECTION AND USER PRIORITIZATION FOR CONTROL," Ser. No. 10/956,435, all of which are herein incorporated by reference, describe some of the difficulties encountered in healthcare workspaces.

Some healthcare workspaces, such as the operating room and radiology, have space restrictions. Proliferation of gadgetry may cause overcrowding. Due to the risk of overcrowding, the addition of equipment and imaging systems becomes less feasible. This is especially true if a new equipment or imaging system does not replace or reduce existing equipment. A cluttered workspace may lead to inefficiency.

An additional drawback of equipment proliferation is the lack of integration. Healthcare practitioners may prefer to have an integrated source for image data, rather than several different sources. However, a piecemeal approach to equipment acquisition and a lack of standardization between components may lead to a proliferation of separate image data sources in a healthcare workspace. This may require a healthcare worker, such as a radiologist or surgeon, to view image data on multiple pieces of equipment.

A PACS system may recall and display historical patient image data on a PACS workstation. It is understood that the term historical, as used in this application, does not require that the image data be of a certain vintage. Instead, it merely refers to image data acquired from a patient during a past procedure. A past procedure, in turn, could include procedures recently performed, such as those performed earlier during the day, or even within seconds. For example, during an emergency, a patient may be imaged by a prior imaging device, and then rushed into an operating room where there is a PACS workstation. The image data from the prior imaging device may be historical image data and displayable on the PACS workstation, even though it was acquired within minutes, or even seconds. A PACS workstation may be provided in a healthcare workspace to assist a healthcare worker to provide access to historical image data. Healthcare professionals who are treating or imaging patients may appreciate flexible access to a patient's medical image history. For example, a surgeon performing a procedure may appreciate having a patient's historical medical image data available in the operating room. As another example, a radiologist may also appreciate having a patient's medical image data available during the imaging procedure. Similarly, a healthcare professional may appreciate having access to other patient's image data during a procedure or examination. To this end, a PACS workstation may be provided in a healthcare workspace to provide flexible access to historical patient image data.

However, the addition of a PACS workstation may crowd a healthcare workspace. Additionally, it may lead to increasing decentralization of patient image data. For example, a radiologist may have to look at an ultrasound system to view substantially live image data, and at a separate PACS workstation to view historical image data. Additionally, a radiologist may have to view multiple monitors, or multiple PACS workstations to view relevant images. A proliferation of image data sources may lead to a lowered manageability of image data.

Additionally, medical image data may not be provided in a DICOM-compliant format. As a result, a PACS station may not be able to display or otherwise render non-compliant images. Images that are not DICOM-compliant may not be properly stored and retrieved in a PACS system. For example, medical imaging devices, such as an ultrasound or endoscope, may not provide image data in a DICOM-compliant format. Instead, such devices may only provide non-compliant images. This can lead to fragmented archival systems—one system archiving and retrieving DICOM-compliant images, and other systems for archiving and retrieving non-compliant formats.

Thus, there is a need for systems that reduce clutter in a healthcare workplace. Additionally, there is a need for systems that assist in the integration of medical image data sources. There is a need for systems that integrate image data not provided a DICOM-compliant format into a PACS system. Moreover, there is a need for a system and method which provide integrated display of substantially live and historical images.

BRIEF SUMMARY OF THE INVENTION

Certain embodiments of the present application provide a healthcare imaging system including a first image feed having at least one historical image, a second image feed having at least one substantially live image, and an application executable on a Picture Archiving and Communication System workstation, wherein the application is capable of processing in real-time the first image feed and the second image feed to provide an integrated display of both the historical images and the substantially live images. In an embodiment, the integrated display is customizable. In an embodiment, the at least one historical image is DICOM-compliant. In an embodiment, the substantially live image is DICOM-compliant. In an embodiment, the system further includes a DICOM-compliance module for conforming the at least one substantially live image to a DICOM-compliant format. In an embodiment, the at least one substantially live image represents data obtained by at least one of: an ultrasound system; an endoscope; a C-arm; a guided surgical unit; and a robotic sensor. In an embodiment, the second image feed is recordable by the application to form a recorded feed. In an embodiment, the recorded feed is DICOM-compliant.

Certain embodiments of the present application provide a method for imaging in a healthcare environment including receiving in an application a first feed, the first feed including historical patient image data; receiving in the application a second feed, the second feed including substantially live patient image data; and integrating in real-time in the application the first feed and the second feed to form a display representation, the display representation displayable on a display, and the display representation simultaneously including data corresponding to the first feed and the second feed. In an embodiment, the application is executable on a Picture Archiving and Communication System workstation. In an embodiment, the display representation is customizable. In an embodiment, the historical patient image data includes a DICOM-compliant format. In an embodiment, the substantially live patient image data includes a DICOM-compliant format. In an embodiment, the method further includes an image converter for converting the substantially live patient image data into a DICOM-compliant format. In an embodiment, the substantially live patient image data represents data from at least one of: an ultrasound system; an endoscope; a C-arm; a guided surgical unit; and a robotic sensor. In an embodiment, the second feed is recordable in a DICOM-compliant format.

Certain embodiments of the present application provide imaging system for healthcare environments including: an application executable on a Picture Archiving and Communication System workstation; and substantially live image data communicatively coupled to the application, the substantially live image data recordable by the application to form recorded image data. In an embodiment, the system further includes a translation module for providing the substantially live image data in a DICOM-compliant format. In an embodiment, the substantially live image data comprises a DICOM-compliant format. In an embodiment, the substantially live image data represents data from at least one of: an ultrasound system; an endoscope; a C-arm; a guided surgical unit; and a robotic sensor. In an embodiment, the application provides in real-time displayable data including the substantially live image data. In an embodiment, the system further includes stored image data communicatively coupled to the Picture Archiving and Communication System workstation, wherein the application processes in real-time the stored image data and the substantially live image data to form integrated displayable data. In an embodiment, the integrated displayable data is customizable.

Certain embodiments of the present application provide a computer-readable storage medium including a set of instructions for a computer, the set of instructions including: a first receiving routine for receiving a first feed, the first feed comprising historical patient image data; a second receiving routine for receiving a second feed, the second feed comprising substantially live patient image data; and a processing routine for integrating data in real-time corresponding to the first feed and the second feed to form an integrated display representation. In an embodiment, the further includes a recording routine for recording at least a portion of the second feed. In an embodiment, at least one of said first receiving routine, second receiving routine, processing routine, and recording routine are executable on a Picture Archiving and Communication System workstation.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
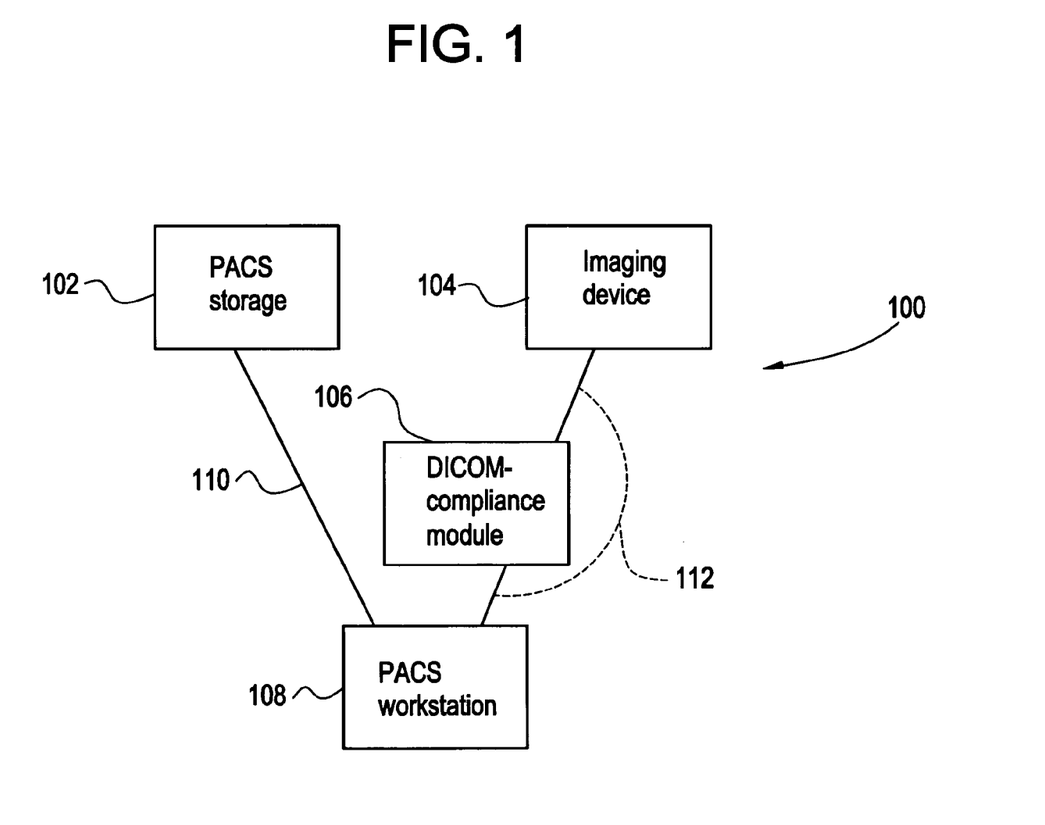
FIG. 1 shows a block diagram of a medical imaging system according to an embodiment of the present application.

FIG. 1 shows a block diagram of a medical imaging system 100 according to an embodiment of the present application. The medical imaging system 100 may include a PACS storage 102. A PACS storage 102 comprises storage media capable of storing DICOM-compliant image data. The storage media may be any digital media suitable for storing DICOM-compliant image data. For example, a PACS storage 102 may include a PACS long-term archive. A PACS long-term archive may contain, for example, patients' historical medical image data. As another example, a PACS storage 102 may include a PACS short-term archive which also may contain patients' historical medical image data. A PACS storage may also contain non-image data, for example. Historical medical image data may include two or three dimensional image data of a patient. Historical medical image data may also include static image data, streaming image data, video image data, or the like.

PACS storage 102 is in electronic communication with a PACS workstation 108 over a communication pathway 110. The PACS workstation 108 may electronically communicate, so that medical image data is communicated across the pathway 110 from the PACS storage 102 to the PACS workstation 108. The PACS workstation 108 may have local storage to retain medical image data communicated from the PACS storage 102. The communication pathway 110 may provide persistent communication channel(s), or the communication channel(s) between the PACS workstation 108 and the PACS storage 102 may be intermittent. It is understood that any communication pathway, such as communication pathway 110 or 112, may comprise a wired network, an optical network, a wireless network, or a combination thereof.

The medical imaging system 100 also may include an imaging device 104. The imaging device 104 produces substantially live image data of a patient. For example, an imaging device 104 may be an ultrasound system, endoscope, x-ray system, CT scanner, C-arm system, guided surgical unit, robotic sensor, or the like. For example, an imaging device 104 may be used during inpatient or outpatient surgical procedures. As another example, an imaging device 104 may be used by radiologists. An imaging device 104 may produce two or three dimensional substantially live image data of a patient. An imaging device 104 may produce a sequence of substantially live image data of a patient to form a video, cine, loop, or the like. Substantially live image data, as used in this application, corresponds to data recently acquired, but need not be data corresponding to up-to-the-second data. For example, an imaging device 104 may capture image data a period of time before providing substantially live image data. Delays may be expected due to various factors including image-processing bottlenecks and network traffic. As another example, an imaging device 104 may function in a manner similar to a digital camera or digital camcorder. In this scenario, the imaging device 104 may locally store one or more still images and/or videos, and later upload the substantially live image data. Thus, it should be understood that substantially live image data encompasses a wide variety of image data, including image data acquired a period of time before uploading.

An imaging device 104 may provide DICOM-compliant image data. If the images are DICOM-compliant, then substantially live images may be communicated from an imaging device 104 to a PACS workstation 108 across a communication pathway 112 (illustrated by the dotted line in FIG. 1). However, an imaging device 104 may also provide image data that is not DICOM-compliant. If the images are not DICOM-compliant, then substantially live images may be communicated across a communication pathway 112 from an imaging device 104 to a DICOM compliance module 106. A DICOM compliance module 106 may receive non-compliant image data. The DICOM compliance module 106 may transform, transcode, format, transpose, or otherwise adapt the non-compliant image data into corresponding DICOM-compliant image data. The DICOM compliance module 106 may be implemented as a part of a PACS workstation 108. Alternatively, the DICOM compliance module 106 may be implemented as part of an imaging device 104. As yet another option, the DICOM compliance module 106 may be a separate network device, or it may be implemented in a distributed manner across various network components.

Figure 2:
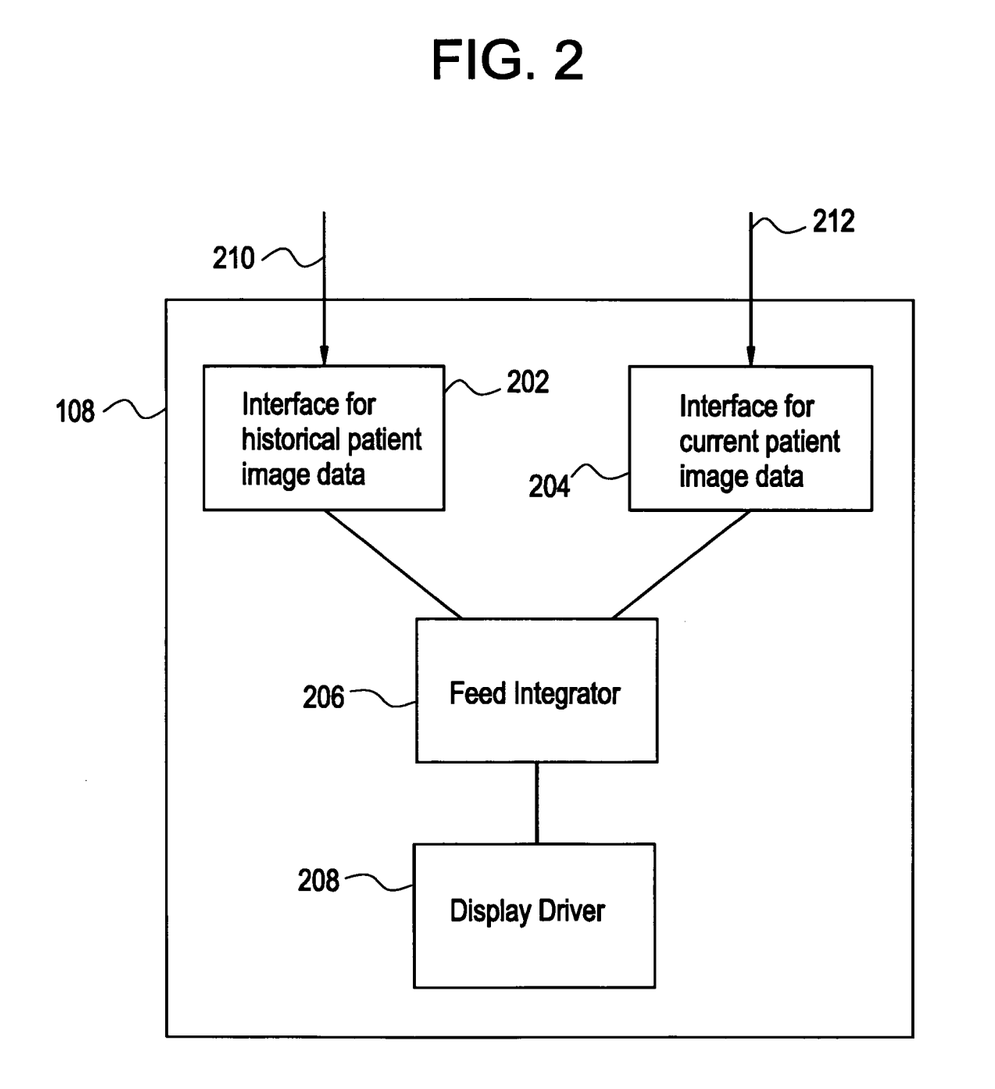
FIG. 2 shows a block diagram of a PACS workstation according to an embodiment of the present application.

FIG. 2 shows a block diagram of a PACS workstation 108 according to an embodiment of the present application. A feed containing historical patient image data 210 may be received at a first interface 202. A feed containing substantially live patient image data 212 may be received at a second interface 204. A feed may include streaming image data, video image data, static image data, two dimensional image data, three dimensional image data, or the like, or any combination thereof. If a feed includes static image data, the image may be periodically or occasionally refreshed or retransmitted. However, it is also possible for a feed to include only one transmission instance of a static image. According to an embodiment, the historical feed (210) and substantially live feed (212) may be multiplexed on to one communications channel or line and received by a unitary interface, and then demultiplexed.

The interfaces 202 and 204 are communicatively linked to a feed integrator 206. The feed integrator 206 may integrate the historical image data and substantially live image data to form displayable image data comprising both past time image data and substantially live image data. The feed integrator 206 may be capable of performing integration in real-time. The feed integrator 206 may also be capable of integrating additional image and non-image data. For example, feed integrator 206 may also be capable of integrating data corresponding to patient blood pressure, pulse, and other vital signs. The feed integrator 206 may integrate this additional data into displayable image data.

The displayable image data may further be communicated to display driver 208 for displaying integrated image data. According to an embodiment, the historical image data is substantially the same throughout the period of integration. For example, image data integration may be used for surgical purposes. A doctor may wish to see a historical x-ray of the patient's lung cavity, and have that historical image integrated along side a substantially live endoscope view of the patient during surgery. In this situation, the substantially live image data changes as the endoscope is navigated inside the patient. However, the historical data is static. It may be preferable to store historical image data in local digital storage media so feed integrator 206 may rapidly access historical image data. Consequently, it may be preferable to include digital storage media in feed integrator 206, or in PACS workstation 108. Digital storage media may also be useful for buffering and recording feeds.

Figure 3:
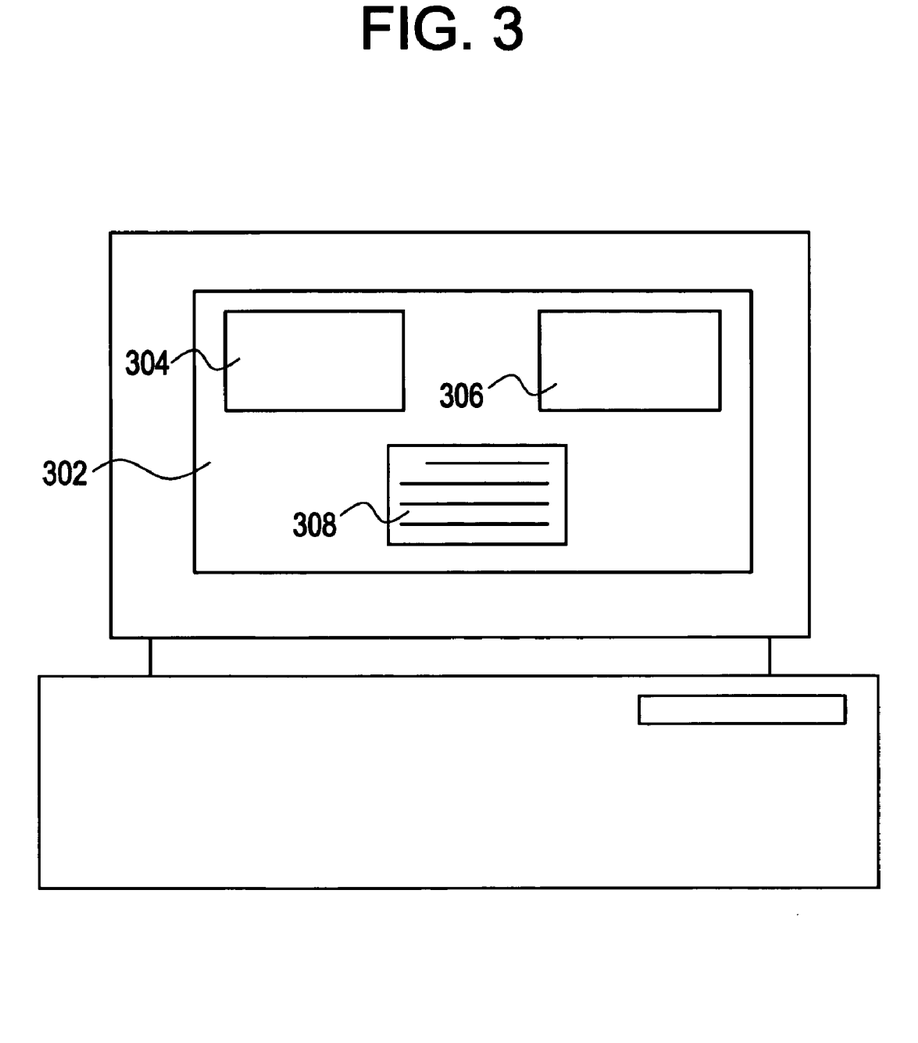
FIG. 3 shows a representation of an integrated display on a PACS workstation according to an embodiment of the present application.

FIG. 3 shows a representation of an integrated display on a PACS workstation 108 according to an embodiment of the present application. PACS workstation 108 comprises a display 302. The display comprises historical image data representation 304 and substantially live image data representation 306. The display 302 is capable of simultaneously displaying both historical image data representation 304 and substantially live image data representation 306. The image data representations 304 and 306 may be displayed, for example, in a single application. Alternatively, the image data representations 304 and 306 may be displayable as part of separate applications.

A user of a PACS workstation 108 may be able to reconfigure or rearrange the positions and sizes of the image data representations 304 and 306. One potential way to reconfigure and rearrange the image data representations 304 and 306 is through perspectives as disclosed in U.S. Patent Application "SYSTEM AND METHOD FOR RULES-BASED CONTEXT MANAGEMENT IN AN MEDICAL ENVIRONMENT," filed on Oct. 1, 2004. At a minimum, perspectives provide a way to flexibly configure and arrange medical information. An application can employ perspectives to integrate various data for simultaneous viewing by a user.

A user of a PACS workstation 108 may also be able to integrate each of image data representations 304 and 306 with non-image data 308. Non-image data may include, for example, patient vital information such as blood pressure, temperature, and pulse. Various non-image data 308 may be separately arrangeable with respect to other of non-image data 308 and image data representations 304 and 306.

Additionally, a user may also be able to edit image data parameters such as color, contrast, sharpness, image quality, and other well-known image data parameters. The editable image data parameters may correspond to each, or both of image data representations 304 and 306.

Figure 4:
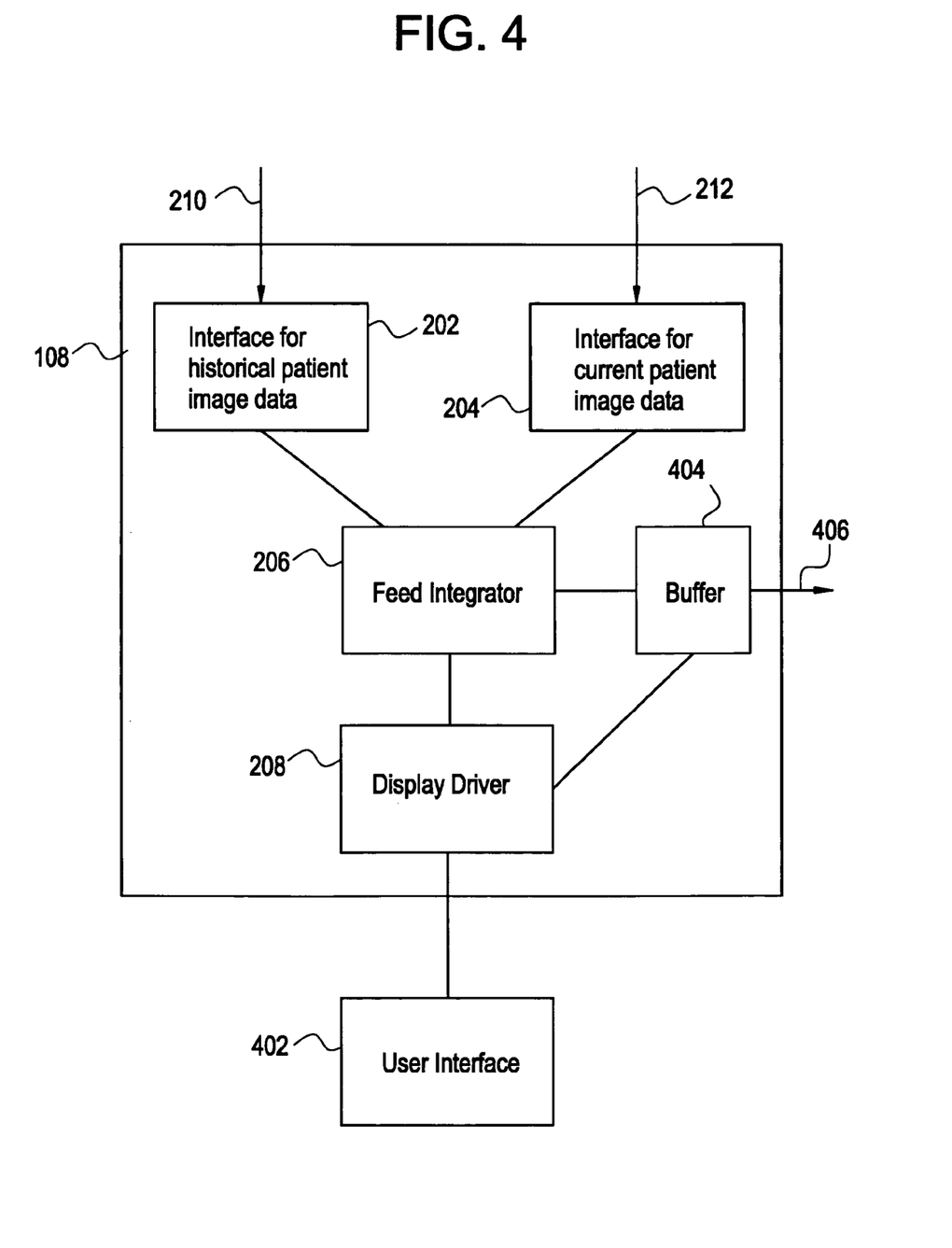
FIG. 4 shows a block diagram of a PACS workstation employing recording capability according to an embodiment of the present application.

FIG. 4 shows a block diagram of a PACS workstation 108 employing recording capability according to an embodiment of the present application. A user interface 402 is shown in communication with PACS workstation 108. A user interface 402 may include, for example, a keyboard, mouse, or the like. A user may control the PACS workstation 108 through user interface 402 to record substantially live image data. The PACS workstation 108 may also automatically record substantially live image data. PACS workstation 108 includes a substantially live image data recording buffer 404. The buffer 404 may include digital storage media. More generally, the workstation 108 may include digital storage media. The buffer 404 may store the substantially live image data in a DICOM-compliant format. The buffer 404 may be communicatively linked with a PACS network to export the stored substantially live image data 406 at a remote location on the PACS network.

Figure 5:
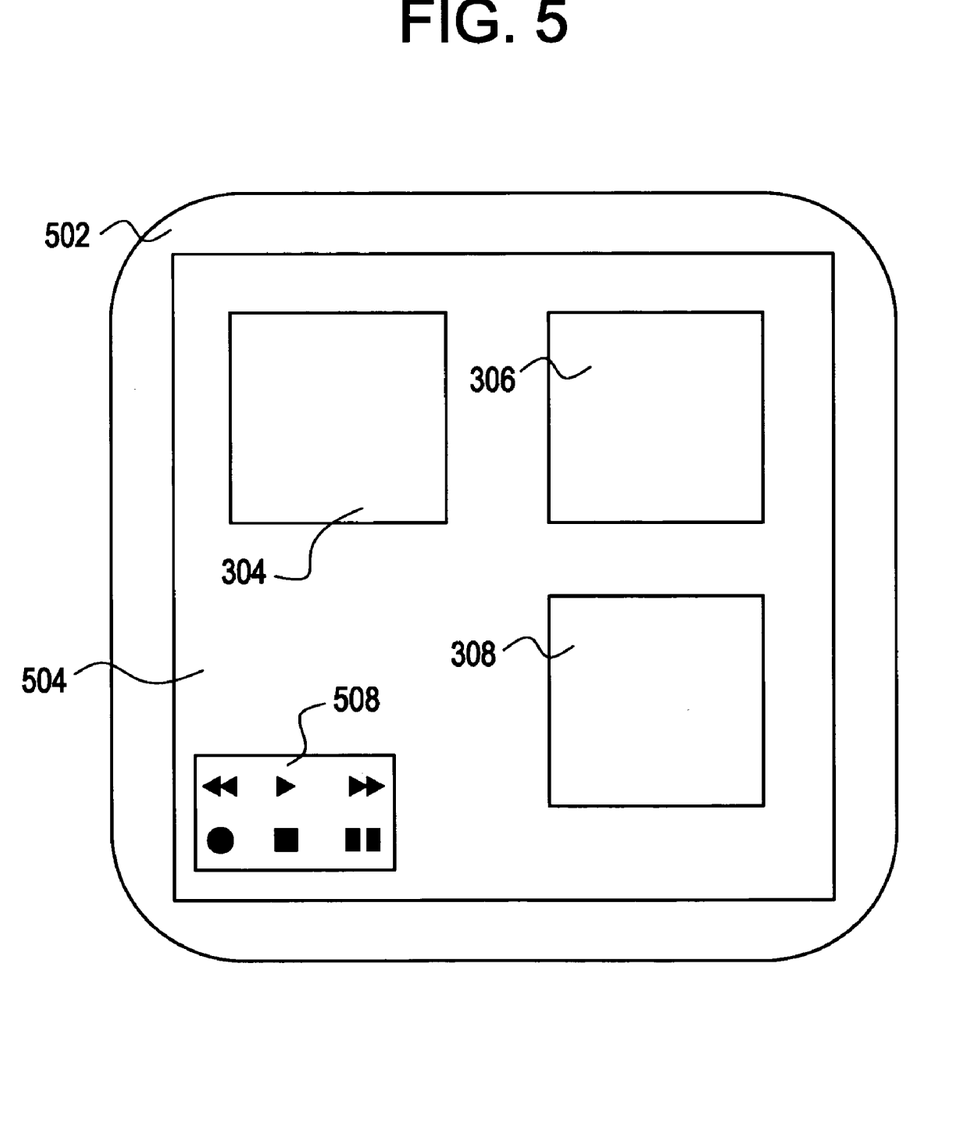
FIG. 5 shows a display of a PACS workstation in accordance with an embodiment of the present application.

FIG. 5 shows a display of a PACS workstation 108 in accordance with an embodiment of the present application. Display 502 includes an application frame 504. Application frame 504 may include historical image data representation 304 and substantially live image data representation 306. Application frame 504 may also include non-image data 308, such as patient vital information, patient name, or patient allergies. Various combinations of non-image data 308 may be selected for display, with various arrangements. The historical image data representation 304, substantially live image data representation 306, and non-image data 308 may be arranged, sized, configured, and displayed in various configurations. The data 304, 306, and 308 may be arrangeable by using perspectives. Any given configuration of data 304, 306, and 308 may be saved and recallable. A variety of configurations may be readily available to a user, and may rapidly change based on principles of work-flow or gaze-detection, for example.

Application frame 504 also includes recording and/or playback controls 508. Recording and/or playback controls 508 may be in a separate panel, represented by icons, menus, radio buttons, check boxes, drop-down menus, or any of a variety of other ways to indicate recording controls. Recording and/or playback controls 508 may be indicated by icons other than those shown in FIG. 5. A user may actuate a recording and/or playback control 508 to start or stop recording, rewind, fast-forward, pause, or play, for example. Other possibilities include frame advance, frame reverse, adjust playback speed, and various other well-known video playback and/or editing modes. Recording and/or playback controls 508 may only include a subset of such modes, such as, for example, only recording and stop recording controls.

Recording and/or playback controls 508 may be used to record data. For example, a user may select a recording control 508 to start recording by clicking an icon, thereby initiating the recording process. As another option, recording may begin automatically based on an event. For example, recording may begin automatically when substantially live image data is detected. There are various possible recording modes. For example, one recording mode may capture the substantially live image data representation 306 as a still image or a video. As another example, a recording mode may capture substantially live image data representation 306 and historical image data representation 304 into one still image or video, or as separate still images or video. As another example, a recording mode may capture non-image data 308 in addition to image data 304, 306 as a still image or video. As another example, a recording mode may capture non-image data 308 as image data header information to accompany a captured image for image data 304, 306.

The data may be captured in a DICOM-compliant format. As another option, the data may be captured in a format that is not DICOM-compliant. In this scenario, it may be useful to later convert the image data into a DICOM-compliant format. It may be preferable, for example, to receive a non-DICOM-compliant data feed corresponding to the substantially live image data representation 306. The non-DICOM-compliant data may be displayed and captured into memory, and later converted to a DICOM-compliant format after, or during the recording process.

The process of recording includes storing data in a digital media storage, such as an optical disk, a magnetic disk, a random access memory, a flash memory, or the like. For example, the process of recording may include storing image data in buffer 404 (shown in FIG. 4). As another option, recording may include transferring image data from buffer 404 into another digital media storage, such as a magnetic hard disk. As another option, recording may include transferring image data from a magnetic hard disk located locally at the PACS workstation to another digital media storage. A digital media storage may be located locally at a PACS workstation 108, or may be located remotely across a communication pathway.

The ability to record enables a user to capture an entire episode or a portion of an episode of imaging. For example, the recording feature allows a user to record an entire surgical procedure, and save the resulting image in a DICOM-compliant format. The resulting recorded image data may be stored and associated with other of patient data in a PACS system. For example, the recorded image data may be stored in association with a patient's historical image data and/or in association with a patient's non-image data.

Playback controls 508 may actuate different modes of playback. For example, by clicking on a rewind icon, the data 304, 306, and/or 308 may be displayed in a reverse time-sequence fashion. Time-sequence data may be stored in a buffer 404, or in digital storage media, such as a local digital storage media.

As an illustrative example, embodiments of the present application may be used in the following manner. A PACS workstation 108 is connected through communications channel to a PACS archive 102. The PACS archive 102 contains historical patient image data, including relevant x-ray data. The relevant x-ray data is communicated to the PACS workstation. The PACS workstation 108 also receives substantially live image data. The substantially live image data is generated by an endoscope that does not provide DICOM-compliant images. The endoscope data is further processed by a DICOM-compliance module to ensure that the image data is in a DICOM-compliant format. The endoscope data is then received by the PACS workstation 108, and stored in a buffer 404 on the PACS workstation.

After receiving both the historical x-ray data and substantially live endoscope data, a feed integrator 206 integrates the x-ray and endoscope image data into an integrated feed. The integrated feed is passed to a display driver 208, and it is displayed to a user. A user through a user interface 402 may configure the arrangements, sizes, and orientations of the x-ray and endoscope images. Thus, both historic and substantially live image data are integrated and displayed.

The user then can start recording the image data through the use of the recording controls 508. The user can record the endoscope data only, and save this in a DICOM-compliant format. Thus, images from a surgical episode can be recorded and saved. The recorded endoscope data is then stored in association with the patient's historical data, including the x-ray data.

Figure 6:
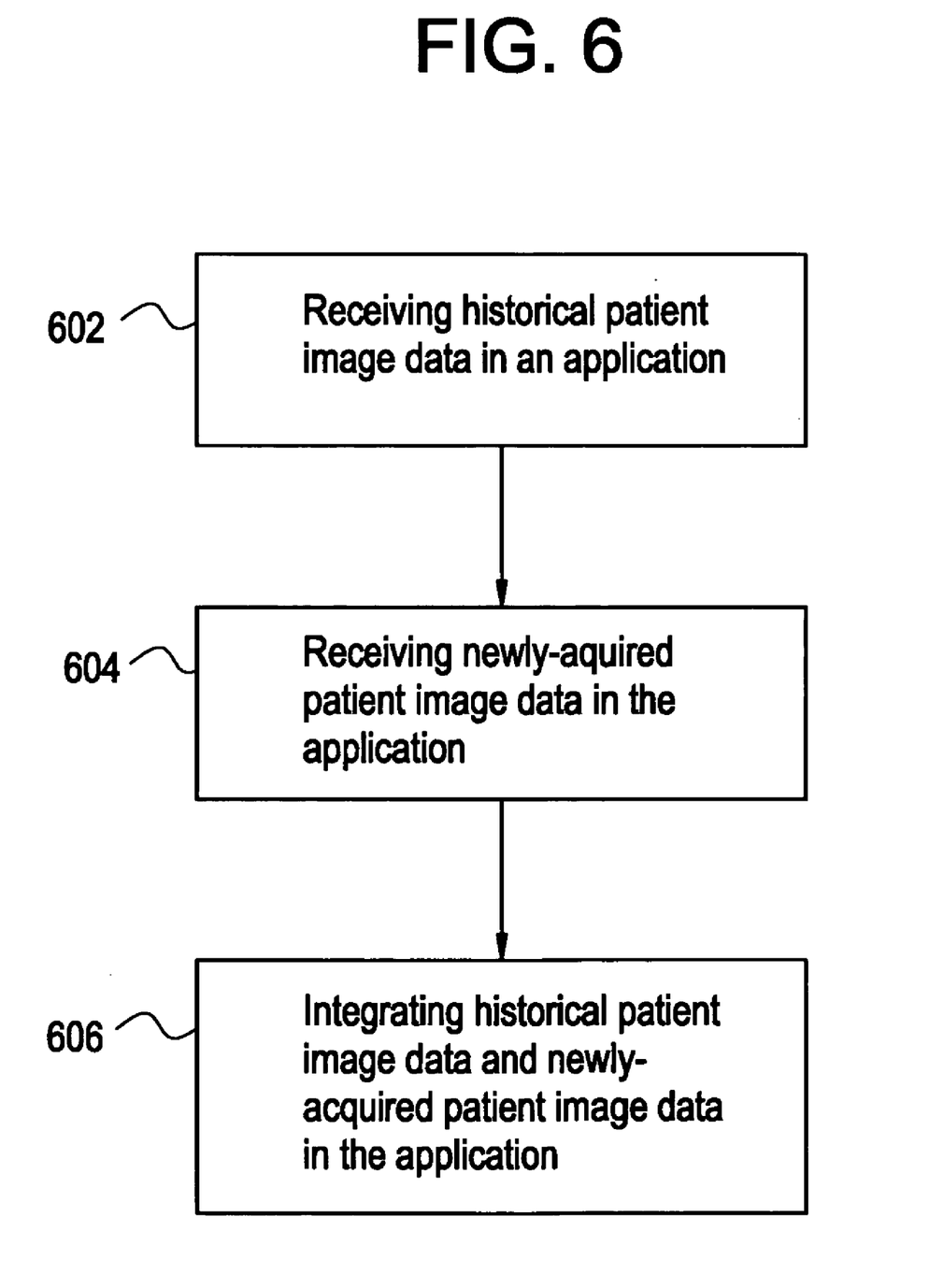
FIG. 6 shows a flowchart of a method for integrating image data in accordance with an embodiment of the present application.

FIG. 6 shows a flowchart in accordance with an embodiment of the present application. At step 602, an application receives historical patient image data. At step 604, the application receives substantially live patient image data. Step 604 may be performed before, after, or contemporaneously with step 602. At step 606, the substantially live image data and historical image data are integrated by the application.

As an illustrative example, a surgical assistant operates a PACS workstation in an operating room during a patient's procedure. An application runs on the PACS workstation. The application is employed to receive from a PACS storage (shown as 102 in FIG. 1) an x-ray that was generated earlier that day. The application also receives a substantially live image data feed of the patient from an endoscope system that probes the patient during surgery. The application then integrates the endoscope feed and the x-ray image data. The integrated data may subsequently be displayed.

Thus, embodiments of the present application reduce clutter in a healthcare workplace. Additionally, embodiments of the present application provide assistance in the integration of medical image data sources. Embodiments of the present application integrate image data not provided a DICOM-compliant format into a PACS system. Moreover, embodiments of the present application provide integrated display of substantially live and historical images.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A healthcare imaging system comprising:
   a first image feed comprising at least one historical image;
   a second image feed comprising at least one substantially live image;
   a compliance module configured to conform said at least one substantially live image to a format compliant with the Digital Imaging and Communications in Medicine standard (DICOM); and
   an application configured to be executed on a Picture Archiving and Communication System workstation;
   wherein said application is configured to process in real-time said first image feed and said second image feed, and is configured to provide an integrated display of both said historical and substantially live images; and
   wherein said at least one substantially live image represents data obtained by at least one of an ultrasound system, an endoscope, a C-arm; a guided surgical unit, or a robotic sensor.

2. The system of claim 1, wherein said integrated display is configured to be customizable.

3. The system of claim 1, wherein said at least one historical image is DICOM-compliant.

4. The system of claim 1, wherein said at least one substantially live image is DICOM-compliant.

5. The system of claim 1, wherein said second image feed is configured to be recorded by said application to form a recorded feed.

6. The system of claim 5, wherein said recorded feed is DICOM-compliant.

7. A method for imaging in a healthcare environment comprising:
   receiving in an application a first feed, said first feed comprising historical patient image data;
   receiving in said application a second feed, said second feed comprising substantially live patient image data;
   integrating in real-time in said application said first feed and said second feed to form a display representation, wherein said display representation simultaneously includes data corresponding to said first feed and said second feed; and
   converting said substantially live patient image data into a format compliant with the Digital Imaging and Communications in Medicine standard (DICOM);
   wherein said substantially live patient image data represents data from at least one of an ultrasound system, an endoscope, a C-arm, a guided surgical unit, or a robotic sensor.

8. The method of claim 7, further comprising executing said application on a Picture Archiving and Communication System workstation.

9. The method of claim 7, further comprising customizing said display representation.

10. The method of claim 7, wherein said historical patient image data comprises a DICOM-compliant format.

11. The method of claim 7, wherein said substantially live patient image data comprises a DICOM-compliant format.

12. The method of claim 7, further comprising recording said second feed in a DICOM-compliant format.

13. A non-transitory computer-readable storage medium including a set of instructions for a computer, the set of instructions comprising:
   a first receiving routine configured to receive a first feed, said first feed comprising historical patient image data;
   a second receiving routine configured to receive a second feed, said second feed comprising substantially live patient image data;
   a processing routine configured to integrate data in real-time corresponding to said first feed and said second feed to form an integrated display representation; and
   a translation routine configured to provide said substantially live patient image data in a format compliant with the Digital Imaging and Communications in Medicine standard (DICOM);

wherein said substantially live patient image data represents data from at least one of an ultrasound system, an endoscope, a C-arm, a guided surgical unit, or a robotic sensor.

14. The computer-readable storage medium of claim 13 further comprising a recording routine configured to record at least a portion of said second feed.

15. The computer-readable storage medium of claim 14, wherein at least one of said first receiving routine, second receiving routine, processing routine, and recording routine are configured to execute on a Picture Archiving and Communication System workstation.

16. The computer-readable storage medium of claim 13, wherein a layout of said integrated display representation is configured to be customized.

* * * * *